(12) United States Patent
Hong et al.

(10) Patent No.: US 11,222,729 B2
(45) Date of Patent: Jan. 11, 2022

(54) ELECTRONIC DEVICE AND METHOD FOR PROVIDING STRESS INDEX CORRESPONDING TO ACTIVITY OF USER

(71) Applicant: Samsung Electronics Co., Ltd., Suwon-si (KR)

(72) Inventors: Hyun Su Hong, Seongnam-si (KR); Sang Beom Nam, Suwon-si (KR); Yong Jin Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 602 days.

(21) Appl. No.: 16/146,263

(22) Filed: Sep. 28, 2018

(65) Prior Publication Data

US 2019/0115107 A1 Apr. 18, 2019

(30) Foreign Application Priority Data

Oct. 18, 2017 (KR) .......................... 10-2017-0135227

(51) Int. Cl.
*A61B 5/11* (2006.01)
*G16H 50/30* (2018.01)
(Continued)

(52) U.S. Cl.
CPC ............. *G16H 50/30* (2018.01); *A61B 5/002* (2013.01); *A61B 5/0022* (2013.01);
(Continued)

(58) Field of Classification Search
CPC ..... A61B 5/002; A61B 5/0022; A61B 5/0205; A61B 5/02055; A61B 5/02405;
(Continued)

(56) References Cited

U.S. PATENT DOCUMENTS 8,981,941 B2  3/2015 Takamura et al.
9,133,024 B2  9/2015 Phan et al.
(Continued)

FOREIGN PATENT DOCUMENTS

EP  2581847 A1  4/2013
JP  2007-503958 A  3/2007
(Continued)

OTHER PUBLICATIONS

Japanese Office Action dated Oct. 23, 2019, issued in Japanese Patent Application No. 2018-194004.
(Continued)

*Primary Examiner* — Tammie K Marlen
(74) *Attorney, Agent, or Firm* — Jefferson IP Law, LLP

(57) ABSTRACT

An electronic device is provided that includes a display, a biometric sensor, a motion sensor, a communication circuit configured to receive a signal for obtaining information related to a location of the electronic device, and a processor electrically connected with the display, the biometric sensor, the motion sensor, and the communication circuit, wherein the processor is configured to identify repeated activities related to the user, which follow a lapse of time, based on motion information obtained according to the lapse of time by using the motion sensor and location information obtained according to the lapse of time by using the communication module, calculate a stress index of the user corresponding to the repeated activities based on biometric information obtained by using the biometric sensor, and provide at least one activity of the repeated activities and a stress index corresponding to the at least one activity.

20 Claims, 12 Drawing Sheets

7hr/85%
(SLEEPING TIME/EFFICIENCY)

6.4
(STRESS STRENGTH)

1.8
(STRESS STRENGTH)

2.4
(STRESS STRENGTH)

4.6
(STRESS STRENGTH)

3.0Kcal
(CALORIE)

(51) Int. Cl.
    *H04W 4/02*      (2018.01)
    *A61B 5/16*      (2006.01)
    *A61B 5/00*      (2006.01)
    *A61B 5/0205*    (2006.01)
    *A61B 5/024*     (2006.01)
    *H04W 4/029*     (2018.01)

(52) U.S. Cl.
    CPC ........ *A61B 5/0205* (2013.01); *A61B 5/02055* (2013.01); *A61B 5/02405* (2013.01); *A61B 5/02438* (2013.01); *A61B 5/1112* (2013.01); *A61B 5/1118* (2013.01); *A61B 5/165* (2013.01); *A61B 5/486* (2013.01); *A61B 5/4809* (2013.01); *A61B 5/6898* (2013.01); *A61B 5/7275* (2013.01); *A61B 5/7425* (2013.01); *H04W 4/027* (2013.01); *A61B 5/681* (2013.01); *A61B 5/7282* (2013.01); *A61B 2503/20* (2013.01); *A61B 2560/0242* (2013.01); *A61B 2562/029* (2013.01); *A61B 2562/0219* (2013.01); *A61B 2562/0271* (2013.01); *H04M 2250/12* (2013.01); *H04W 4/029* (2018.02)

(58) Field of Classification Search
    CPC . A61B 5/02438; A61B 5/1112; A61B 5/1118; A61B 5/165; A61B 5/4809; A61B 5/486; A61B 5/6898; A61B 5/7275; A61B 5/7425; A61B 5/681; A61B 5/7282; A61B 2503/20; A61B 2560/0242; A61B 2562/0219; A61B 2562/0271; A61B 2562/029; H04W 4/027; H04W 4/029; H04M 2205/12
    See application file for complete search history.

(56) References Cited

U.S. PATENT DOCUMENTS

| | | |
|---|---|---|
| 9,189,599 B2 | 11/2015 | Adler et al. |
| 9,538,921 B2 | 1/2017 | Leboeuf et al. |
| 9,619,998 B2 | 4/2017 | Takamura et al. |
| 9,978,259 B2 | 5/2018 | Takamura et al. |
| 9,993,189 B2 | 6/2018 | Phan et al. |
| 10,209,779 B2 | 2/2019 | Roh et al. |
| 10,217,351 B2 | 2/2019 | Takamura et al. |
| 10,534,900 B2 | 1/2020 | Cheong et al. |
| 2012/0290215 A1 | 11/2012 | Adler et al. |
| 2014/0275854 A1 | 9/2014 | Venkatraman et al. |
| 2014/0276119 A1 | 9/2014 | Venkatraman et al. |
| 2014/0288436 A1 | 9/2014 | Venkatraman et al. |
| 2014/0288438 A1 | 9/2014 | Venkatraman et al. |
| 2014/0335490 A1 | 11/2014 | Baarman et al. |
| 2015/0120205 A1 | 4/2015 | Jeon et al. |
| 2015/0196256 A1 | 7/2015 | Venkatraman et al. |
| 2016/0027324 A1 | 1/2016 | Wisbey et al. |
| 2016/0029898 A1 | 2/2016 | Leboeuf et al. |
| 2016/0029964 A1 | 2/2016 | Leboeuf et al. |
| 2016/0058376 A1* | 3/2016 | Baek ............... A61B 5/7278 340/870.07 |
| 2016/0063101 A1 | 3/2016 | Kanda |
| 2016/0066828 A1 | 3/2016 | Phan et al. |
| 2016/0260046 A1 | 9/2016 | Cai |
| 2017/0027523 A1 | 2/2017 | Venkatraman et al. |
| 2017/0105667 A1 | 4/2017 | Wei et al. |
| 2017/0119315 A1 | 5/2017 | Leboeuf et al. |
| 2018/0344230 A1 | 12/2018 | Phan et al. |
| 2019/0122537 A1 | 4/2019 | Takamura et al. |
| 2019/0187802 A1 | 6/2019 | Roh et al. |

FOREIGN PATENT DOCUMENTS

| | | |
|---|---|---|
| JP | 2012-249797 A | 12/2012 |
| JP | 2013-250861 A | 12/2013 |
| JP | 2015-84913 A | 5/2015 |
| JP | 2015-160050 A | 9/2015 |
| JP | 2016-48495 A | 4/2016 |
| KR | 10-2015-0099430 A | 8/2015 |
| KR | 10-2015-0105514 A | 9/2015 |
| WO | 2013/086363 A2 | 6/2013 |
| WO | 2017/090810 A1 | 6/2017 |
| WO | 2019-031257 A1 | 2/2019 |

OTHER PUBLICATIONS

Mikhail Sysoev et al., "Noninvasive stress recognition considering the current activity", Personal and Ubiquitous Computing, Springer Verlag, London, GB, vol. 19, No. 7, Oct. 1, 2015 (Oct. 1, 2015), pp. 1045-1052, XP058073104.
Extended European Search Report dated Jan. 14, 2021, issued in European Patent Application 18867910.4-1132.
International Search Report dated Jan. 21, 2019, issued in International Application No. PCT/KR2018/011509.
Japanese Notice of Allowability dated Jul. 7, 2020, issued in Japanese Patent Application No. 2018-194004.
Korean Office Action with English translation dated Sep. 30, 2021; Korean Appln. No. 10-2017-0135227.

* cited by examiner

7hr /85%
(SLEEPING TIME/EFFICIENCY)

6.4
(STRESS STRENGTH)

1.8
(STRESS STRENGTH)

2.4
(STRESS STRENGTH)

4.6
(STRESS STRENGTH)

3.0Kcal
(CALORIE)

ELECTRONIC DEVICE AND METHOD FOR PROVIDING STRESS INDEX CORRESPONDING TO ACTIVITY OF USER

CROSS-REFERENCE TO RELATED APPLICATION(S)

This application is based on and claims priority under 35 U.S.C. § 119(a) of a Korean patent application number 10-2017-0135227, filed on Oct. 18, 2017, in the Korean Intellectual Property Office, the disclosure of which is incorporated by reference herein in its entirety.

BACKGROUND

1. Field

The disclosure relates to a technology of providing information related to stress of a user measured by an electronic device.

2. Description of Related Art

Various types of electronic products have been developed and distributed thanks to the development of the electronic technologies. In particular, in recent years, wearable devices, such as smart watches or smart glasses, which may be mounted by users, together with mobile devices, such as smartphones or tablet personal computers (PCs), have been increasingly distributed.

The electronic devices, such as the mobile devices and the wearable devices, may provide various functions for managing health by using sensors embedded in the electronic devices. For example, the electronic devices may provide the users with information on the stresses of the users such that the users may manage the stresses.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a device and a method for providing information related to stress of a user of an electronic device in a form associated with everyday lives of the user.

The electronic devices may measure stress indices of a user by using the embedded sensors and may provide progresses of changes of the stress indices over time. However, the electronic devices cannot suggest the associations between the situations and the stress indices of the user, such as locations and/or activities of the user. Accordingly, the user cannot intuitively recognize the situations in which the users receive stresses from the provided information, and the electronic devices cannot provide the users with appropriate measures for addressing stress.

Additional aspects will be set forth in part in the description which follows and, in part, will be apparent from the description, or may be learned by practice of the presented embodiments.

In accordance with an aspect of the disclosure, an electronic device is provided. The electronic device includes a display, a biometric sensor configured to obtain biometric information of a user of the electronic device, a motion sensor configured to obtain information related to a motion of the electronic device, a communication circuit configured to receive a signal for obtaining information related to a location of the electronic device, and a processor electrically connected with the display, the biometric sensor, the motion sensor, and the communication circuit, wherein the processor is configured to identify repeated activities related to the user, which follow a lapse of time, based on motion information obtained according to the lapse of time by using the motion sensor and location information obtained according to the lapse of time by using the communication module, calculate a stress index of the user corresponding to the repeated activities related to the user based on biometric information obtained by using the biometric sensor, and provide at least one activity of the repeated activities related to the user and a stress index corresponding to the at least one activity.

In accordance with another aspect of the disclosure, an electronic device is provided. The electronic device includes a sensor module including an acceleration sensor and a heart rate (HR) sensor, a communication circuit configured to receive a signal for measuring a location of the electronic device, a display, and a processor electrically connected with the sensor module, the communication circuit, and the display, and wherein the processor is configured to obtain acceleration information of the electronic device, at least one of HR information or heart rate variability (HRV) information of a user of the electronic device, and location information of the electronic device by using the sensor module and the communication circuit, obtain state information associated with repeated activities of the user of the electronic device based on the acceleration information, the location information, and time information, calculate a stress index of the user of the electronic device according to time based on at least one of the HR information or the HRV information, and provide contents including an association relationship between the state information and the stress index to the display or an external electronic device.

In accordance with another aspect of the disclosure, an electronic device is provided. The electronic device includes a communication circuit configured to communicate with an external device, and a processor that is electrically connected to the communication circuit, wherein the processor is configured to obtain acceleration information of the external device, at least one of HR information or HRV information of a user of the external device, and location information of the external device, obtain state information associated with repeated activities of the user of the external device based on the acceleration information, the location information, and time information, calculate a stress index of the user of the external device according to time based on at least one of the HR information or the HRV information, and provide contents including an association relationship between the state information and the stress index to at least one of a display of the electronic device, the external electronic device or another external device.

According to embodiments of the disclosure, an electronic device and a method by which the user may efficiently manage stress by providing contents that represent a stress index associated with a daily routine of the user may be provided.

In addition, the disclosure may provide various effects that are directly or indirectly recognized.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modification of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
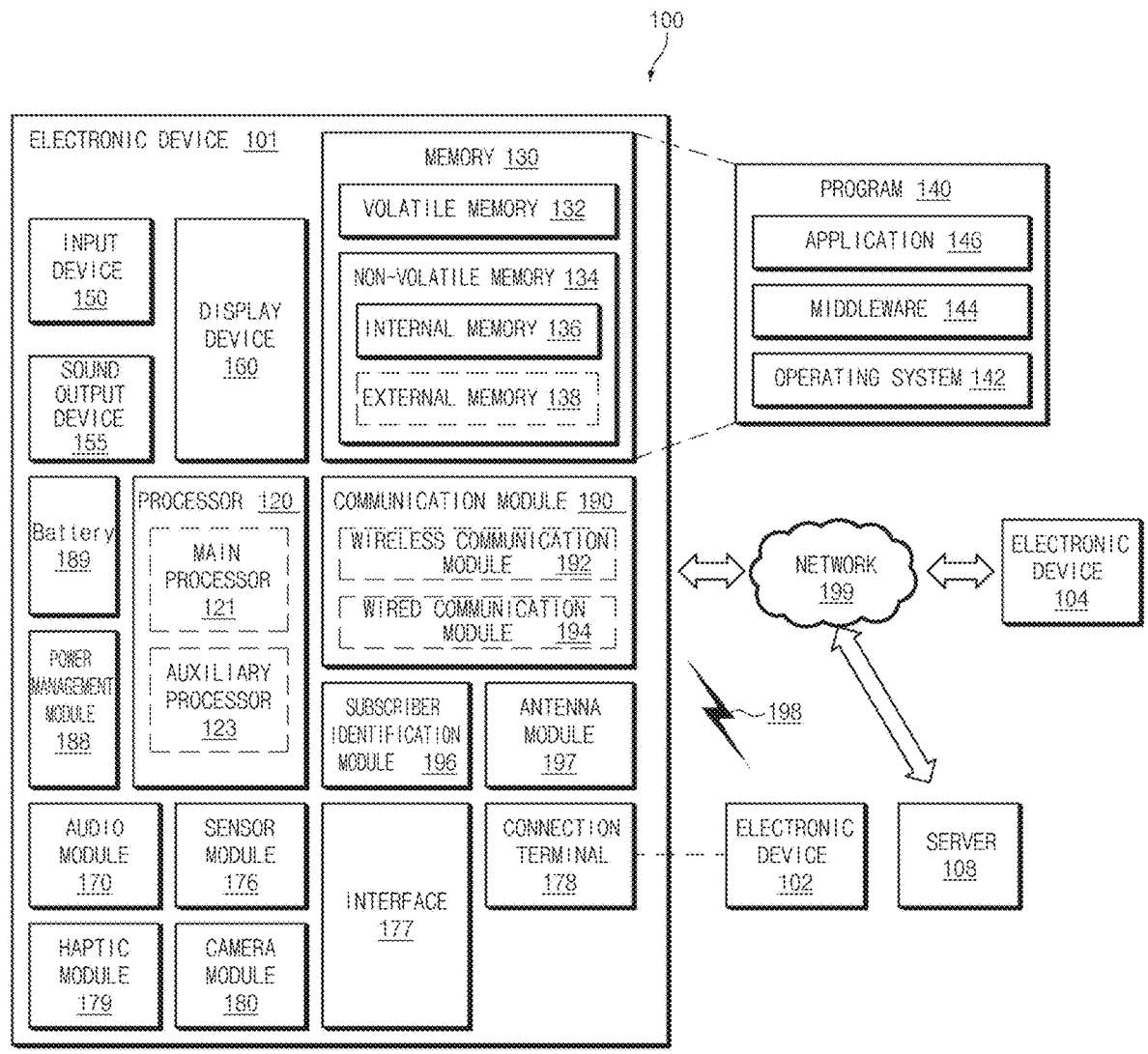
FIG. 1 is a block diagram of an electronic device in a network environment according to an embodiment of the disclosure.

FIG. 1 is a block diagram of an electronic device 101 in a network environment 100 according to an embodiment of the disclosure.

Referring to FIG. 1, the electronic device 101 may communicate with an electronic device 102 through a first network 198 (e.g., a short-range wireless communication) or may communicate with an electronic device 104 or a server 108 through a second network 199 (e.g., a long-distance wireless communication) in the network environment 100. According to an embodiment, the electronic device 101 may communicate with the electronic device 104 through the server 108. According to an embodiment, the electronic device 101 may include a processor 120, a memory 130, an input device 150, a sound output device 155, a display device 160, an audio module 170, a sensor module 176, an interface 177, a haptic module 179, a camera module 180, a power management module 188, a battery 189, a communication module 190, a subscriber identification module 196, and an antenna module 197. According to some embodiments, at least one (e.g., the display device 160 or the camera module 180) among components of the electronic device 101 may be omitted or other components may be added to the electronic device 101. According to some embodiments, some components may be integrated and implemented as in the case of the sensor module 176 (e.g., a fingerprint sensor, an iris sensor, or an illuminance sensor) embedded in the display device 160 (e.g., a display).

The processor 120 may operate, for example, software (e.g., a program 140) to control at least one of other components (e.g., a hardware or software component) of the electronic device 101 connected to the processor 120 and may process and compute a variety of data. The processor 120 may load a command set or data, which is received from other components (e.g., the sensor module 176 or the communication module 190), into a volatile memory 132, may process the loaded command or data, and may store result data into a nonvolatile memory 134. According to an embodiment, the processor 120 may include a main processor 121 (e.g., a central processing unit or an application processor) and an auxiliary processor 123 (e.g., a graphic processing device, an image signal processor, a sensor hub processor, or a communication processor), which operates independently from the main processor 121, additionally or alternatively uses less power than the main processor 121, or is specified to a designated function. In this case, the auxiliary processor 123 may operate separately from the main processor 121 or embedded.

In this case, the auxiliary processor 123 may control, for example, at least some of functions or states associated with at least one component (e.g., the display device 160, the sensor module 176, or the communication module 190) among the components of the electronic device 101 instead of the main processor 121 while the main processor 121 is in an inactive (e.g., sleep) state or together with the main processor 121 while the main processor 121 is in an active (e.g., an application execution) state. According to an embodiment, the auxiliary processor 123 (e.g., the image signal processor or the communication processor) may be implemented as a part of another component (e.g., the camera module 180 or the communication module 190) that is functionally related to the auxiliary processor 123. The memory 130 may store a variety of data used by at least one component (e.g., the processor 120 or the sensor module 176) of the electronic device 101, for example, software (e.g., the program 140) and input data or output data with respect to commands associated with the software. The memory 130 may include the volatile memory 132 or the nonvolatile memory 134.

The program 140 may be stored in the memory 130 as software and may include, for example, an operating system 142, a middleware 144, or an application 146.

The input device 150 may be a device for receiving a command or data, which is used for a component (e.g., the processor 120) of the electronic device 101, from an outside (e.g., a user) of the electronic device 101 and may include, for example, a microphone, a mouse, or a keyboard.

The sound output device 155 may be a device for outputting a sound signal to the outside of the electronic device 101 and may include, for example, a speaker used for general purposes, such as multimedia play or recordings play, and a receiver used only for receiving calls. According to an embodiment, the receiver and the speaker may be either integrally or separately implemented.

The display device 160 may be a device for visually presenting information to the user and may include, for example, a display, a hologram device, or a projector and a control circuit for controlling a corresponding device. According to an embodiment, the display device 160 may include a touch circuitry or a pressure sensor for measuring an intensity of pressure on the touch.

The audio module 170 may convert a sound and an electrical signal in dual directions. According to an embodiment, the audio module 170 may obtain the sound through the input device 150 or may output the sound through an external electronic device (e.g., the electronic device 102 (e.g., a speaker or a headphone)) wired or wirelessly connected to the sound output device 155 or the electronic device 101.

The sensor module 176 may generate an electrical signal or a data value corresponding to an operating state (e.g., power or temperature) inside or an environmental state outside the electronic device 101. The sensor module 176 may include, for example, an acceleration sensor, a gyro sensor, a heart rate (HR) measurement sensor, galvanic skin response (GSR) sensor, blood pressure measurement sensor, a barometric pressure sensor, a magnetic sensor, a gesture sensor, a grip sensor, a proximity sensor, a color sensor, an infrared sensor, a skin temperature sensor, a temperature sensor, a humidity sensor, an illuminance sensor, or the other biometric sensors. The heart rate sensor may be classified based on a method, such as electrocardiography (ECG) measurement, photoplethysmography (PPG) measurement, or the like, but, in the disclosure, the heart rate sensor is hereinafter referred to as a "HR sensor" without any distinction.

The interface 177 may support a designated protocol wired or wirelessly connected to the external electronic device (e.g., the electronic device 102). According to an embodiment, the interface 177 may include, for example, an high-definition multimedia interface (HDMI), a universal serial bus (USB) interface, a secure digital (SD) card interface, or an audio interface.

A connection terminal 178 may include a connector that physically connects the electronic device 101 to the external electronic device (e.g., the electronic device 102), for example, an HDMI connector, a USB connector, an SD card connector, or an audio connector (e.g., a headphone connector).

The haptic module 179 may convert an electrical signal to a mechanical stimulation (e.g., vibration or movement) or an electrical stimulation perceived by the user through tactile or kinesthetic sensations. The haptic module 179 may include, for example, a motor, a piezoelectric element, or an electric stimulator.

The camera module 180 may shoot a still image or a video image. According to an embodiment, the camera module 180 may include, for example, at least one lens, an image sensor, an image signal processor, or a flash.

The power management module 188 may be a module for managing power supplied to the electronic device 101 and may serve as at least a part of a power management integrated circuit (PMIC).

The battery 189 may be a device for supplying power to at least one component of the electronic device 101 and may include, for example, a non-rechargeable (primary) battery, a rechargeable (secondary) battery, or a fuel cell.

The communication module 190 may establish a wired or wireless communication channel between the electronic device 101 and the external electronic device (e.g., the electronic device 102, the electronic device 104, or the server 108) and support communication execution through the established communication channel. The communication module 190 may include at least one communication processor operating independently from the processor 120 (e.g., the application processor) and supporting the wired communication or the wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., an local area network (LAN) communication module or a power line communication module) and may communicate with the external electronic device using a corresponding communication module among them through the first network 198 (e.g., the short-range communication network such as a Bluetooth, a Wi-Fi direct, or an infrared data association (IrDA)) or the second network 199 (e.g., the long-distance wireless communication network such as a cellular network, an internet, or a computer network (e.g., LAN or wide area network (WAN)). The above-mentioned various communication modules 190 may be implemented into one chip or into separate chips, respectively.

According to an embodiment, the wireless communication module 192 may identify and authenticate the electronic device 101 using user information stored in the subscriber identification module 196 in the communication network.

The antenna module 197 may include one or more antennas to transmit or receive the signal or power to or from an external source. According to an embodiment, the communication module 190 (e.g., the wireless communication module 192) may transmit or receive the signal to or from the external electronic device through the antenna suitable for the communication method.

Some components among the components may be connected to each other through a communication method (e.g., a bus, a general purpose input/output (GPIO), an serial peripheral interface (SPI), or an mobile industry processor interface (MIPI)) used between peripheral devices to exchange signals (e.g., a command or data) with each other.

According to an embodiment, the command or data may be transmitted or received between the electronic device 101 and the external electronic device 104 through the server 108 connected to the second network 199. Each of the electronic devices 102 and 104 may be the same or different types as or from the electronic device 101. According to an embodiment, all or some of the operations performed by the electronic device 101 may be performed by another electronic device or a plurality of external electronic devices. When the electronic device 101 performs some functions or services automatically or by request, the electronic device 101 may request the external electronic device to perform at least some of the functions related to the functions or services, in addition to or instead of performing the functions or services by itself. The external electronic device receiving the request may carry out the requested function or the additional function and transmit the result to the electronic device 101. The electronic device 101 may provide the requested functions or services based on the received result as is or after additionally processing the received result. To this end, for example, a cloud computing, distributed computing, or client-server computing technology may be used.

Figure 2:
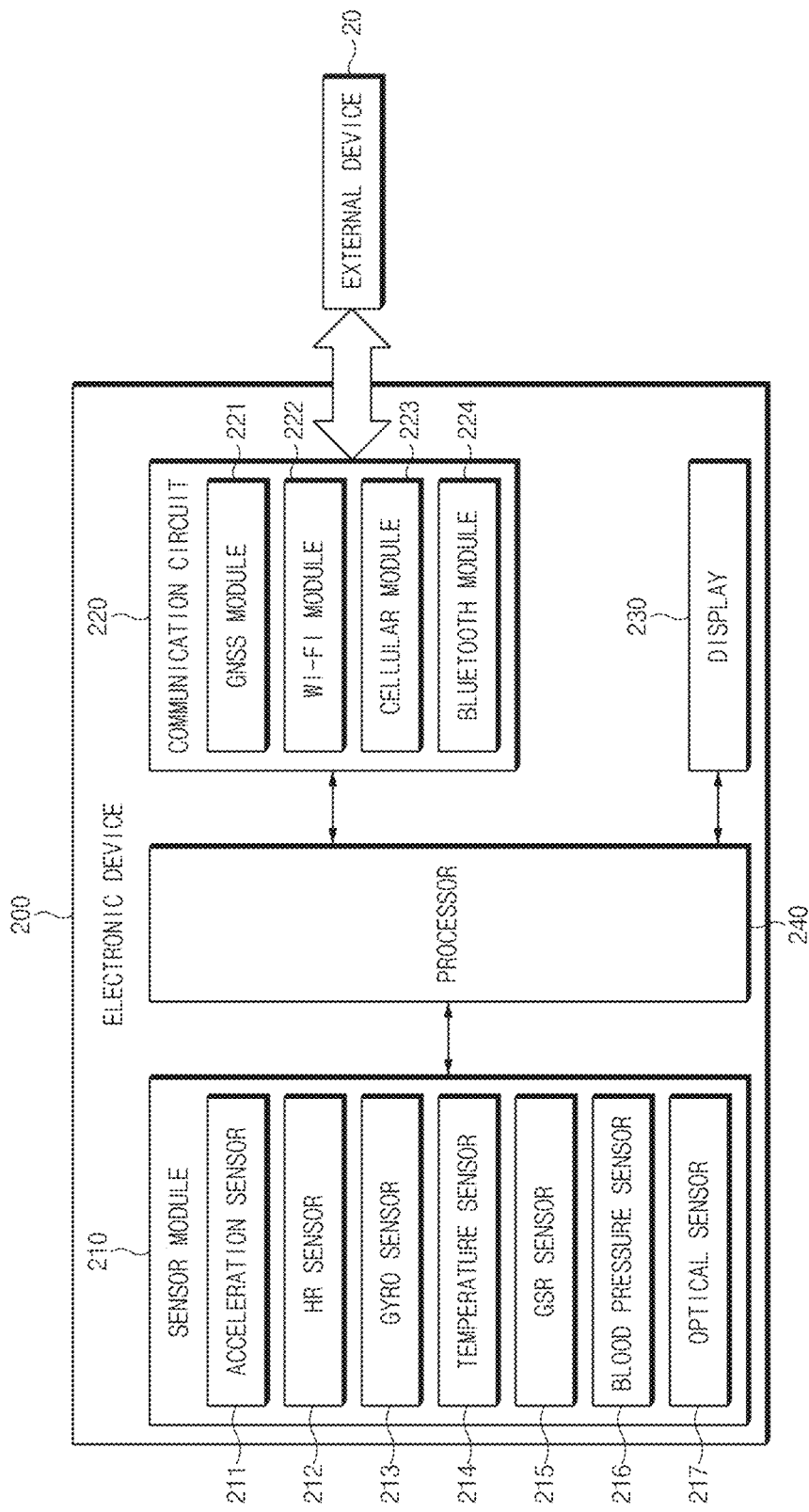
FIG. 2 is a block diagram illustrating a configuration of an electronic device according to an embodiment of the disclosure.

FIG. 2 is a block diagram illustrating a configuration of an electronic device according to an embodiment of the disclosure.

Referring to FIG. 2, an electronic device 200 (e.g., an electronic device 100) may include a sensor module 210 (e.g., a sensor module 176), a communication circuit 220 (e.g., a communication module 190), a display 230 (e.g., a display device 160), and a processor 240 (e.g., a processor 120). The electronic device 200 may be a mobile device in various forms, such as a smartphone or a tablet personal computer (PC), and preferably, may be a wearable device in a form, such as a band, a watch, or glasses that may be always mounted on the body of the user, or may be a server that is connected to a wearable device and/or a mobile device. When the electronic device 200 is a mobile device, the electronic device 200 may not include the sensor module 210. When the electronic device 200 is a server, the electronic device 200 may not include the sensor module 210 and the display 230. When the electronic device 200 is a mobile device or a server, the electronic device 200 may acquire data on the user from the wearable device that may collect and analyze data on the user more easily.

The sensor module 210 may detect information associated with the electronic device 200 or the user. For example, the sensor module 210 may include an acceleration sensor 211 and a HR sensor 212. According to an embodiment, the sensor module 210 may further include at least one of a gyro sensor 213, a temperature sensor 214, a GSR sensor 215, a blood pressure sensor 216, or an optical sensor 217. The sensor module 210 may detect information on some of an acceleration of the electronic device 200, a HR of the user, an angular speed of the electronic device 200, a skin temperature of the user, a skin conductivity of the user, a blood pressure of the user, a blood flow rate of the user, or blood glucose of the user.

The communication circuit 220 may receive a signal for measuring a location of the electronic device 200, and may be configured to communicate with an external electronic device. When the electronic device 200 is a wearable device, the external electronic device may be a server and/or a mobile device. When the electronic device 200 is a mobile device, the external electronic device may be a wearable device and/or a server. When the electronic device 200 is a server, the external electronic device may be a mobile device and/or a wearable device. For example, the communication circuit 220 may include a GNSS module 221 and/or a Wi-Fi module 222. According to an embodiment, the communication circuit 220 may further include at least one of a cellular module 223 and a Bluetooth module 224. For example, the GNSS module 221, the Wi-Fi module 222, or the cellular module 223 may receive a signal for determining a location of the electronic device 200. As another example, the Wi-Fi module 222, the cellular module 223, or the Bluetooth module 224 may perform communication with an external device 20.

The display 230 may output visual information. The display 230, for example, may output contents generated by the electronic device 200 or obtained from the outside.

The processor 240 may be electrically connected to the sensor module 210, the communication circuit 220, and the display 230. The processor 240 may control the sensor module 210, the communication circuit 220, and the display 230, and may perform various data processing and calculations.

The processor 240 may obtain various pieces of information on the electronic device 200 and the user. According to an embodiment, the processor 240 may obtain acceleration information of the electronic device 200, at least one of HR information or HRV information of the user, and location information of the electronic device 200 by using the sensor module 210 and the communication circuit 220. For example, the processor 240 may obtain acceleration information of the electronic device 200 by using the acceleration sensor 211, and may obtain the HR information and/or the HRV information by using the HR sensor 212. The processor 240 may receive location information of the electronic device 200 from the communication circuit 220, and may calculate location information of the electronic device 200 based on the information received from the communication circuit 220. As another example, the processor 240 may obtain angular speed information of the electronic device 200 by using the gyro sensor 213, may obtain skin temperature information of the user by using the temperature sensor 214, may obtain skin conductivity information of the user by using the GSR sensor 215, may obtain blood pressure information of the user by using the blood pressure sensor 216, and may obtain blood glucose information and/or blood flow rate information by using the HR sensor 212 or the additional optical sensor 217. As another example, the processor 240 may obtain information on a use record of the electronic device 200. The processor 240 may receive the above-described information to the external electronic device (e.g., a wearable device). In this case, the user may be a user of the external electronic device.

According to an embodiment, the processor 240 may determine repeated activities related to the user according to lapse of time, based on motion information obtained according to lapse of time by using a motion sensor (e.g., the acceleration sensor 211 and/or the gyro sensor 213) and location information obtained according to lapse of time by using the communication circuit 220. The repeated activities related to the user may include location information and time information corresponding top activities. The processor 240 may determine the repeated activities further based on biometric information. According to an embodiment, the processor 240 may store surrounding environment information of the electronic device 200 in association with the repeated activities related to the user.

The processor 240 may obtain information on a daily routine of the user and a stress index of the user by using the above-described various pieces of information.

According to an embodiment, the processor 240 may obtain state information associated with the repeated activities of the user, based on acceleration information, location information, and time information. The processor 240 may use a pattern of an acceleration signal and a change of a location of the electronic device 200 to obtain state information. According to an embodiment, the processor 240 may use HR information, HRV information, angular velocity information, skin temperature information, skin conductivity information, blood pressure information, blood glucose information, and blood flow rate information of the user, and/or a use record of the electronic device 200 to obtain the state information.

The user may have a repeated daily routine. The processor 240 may obtain state information associated with a repeated activity of the user as the information on the daily routine of the user. According to an embodiment, when the user repeatedly performs the same activity a specified number of times or more in a time section of a specified range, the processor 240 may obtain state information associated with the corresponding activity, the processor 240 may obtain state information associated with the corresponding activity. The processor 240 may identify the type of the activity performed by the user, based on acceleration information, angular speed information, and/or location information. When the user repeatedly performs the same activity a specified number of times or more and a deviation of a time band in which the same activity is performed is smaller than the specified range, the processor 240 may determine the corresponding activity as a daily routine. The processor 240 may obtain information (state information) on the activity that has been determined as a daily routine. For example, the state information may include information on a location at which the corresponding activity is performed, a time at which the corresponding activity is performed, and a type of the corresponding activity.

According to an embodiment, the processor 240 may repeatedly obtain state information that represents whether the user is in a sleeping state, an active state, or an inactive state during a time section of a specified range.

For example, if a change of acceleration information is smaller than a specified value, and/or the HR value is smaller than a specified value, the processor 240 may determine that the user is in a sleeping state. The active state, for example, may refer to a state in which the user performs an activity, such as walking or exercising. If a change pattern of acceleration information is repeated, a change of the acceleration information is larger than a specified value, and/or the HR value is larger than a specified value, the processor 240 may determine that the user is in an active state. The inactive state, for example, may refer to a state in which the user performs an activity, such as a task, a study, a meal, a rest, or movement by a transportation means. If the user is not in a sleeping state or an active state, the processor 240 may determine that the user is in an inactive state.

As another example, the processor 240 may obtain state information further by using location information. For example, the processor may identify a location at which the user stays for a long time as a house, a workplace, or a school, and may obtain state information based on the identified site. The processor 240 may determine a location at which a sleeping state is repeatedly identified as a house. The processor 240 may determine a location to which the user repeatedly moves from the house as a workplace or a school. The processor 240 may identify a movement route between the house and the workplace or the school as a commuting route or a commuting-to-school route. The processor 240 may determine that the user is in a rest state if an inactive state is detected at home, and may identify that the user is in a task state or a study state if an inactive state is detected in the workplace or the school. The processor 240 may determine that the user is in a movement state by a transportation means if an inactive state is detected on a movement route. The processor 240 may determine that the user is in a meal state if an inactive state is detected between a walking movement state from a first point to a second point and a walking movement state from the second point to the first point for 30 minutes to 1 hour. The processor 240 may determine that an inactive state is a meal state if the blood glucose and/or the blood flow rate of the user increases and the inactive state before a specified time period from the corresponding time.

When a sleeping state, an active state (e.g., a walking movement or an exercise), or an inactive state (e.g., a task, a study, a meal, a rest, or movement by a transportation means) is repeatedly identified and a deviation of a time band in which the corresponding state is identified is smaller than a specified range, the processor 240 may determine that the corresponding state corresponds to a daily routine and may obtain state information on the corresponding state.

According to an embodiment, the processor 240 may determine a stress index of the user corresponding to repeated activities related to the user at least based on the obtained biometric information by using a biometric sensor (e.g., the HR sensor 212, the temperature sensor 214, the GSR sensor 215, the blood pressure sensor 216, and/or the optical sensor 217). The biometric sensor may include the HR sensor 212. The processor 240 may determine a stress index, based on at least one of the HR information or the HRV information of the user obtained by using the HR sensor 212.

According to an embodiment, the processor 240 may estimate the stress index of the user by using physiological reaction data of the user measured by the sensor module 210. For example, the processor 240 may calculate a stress index of the user according to time based on at least one of the HR information or the HRV information. The processor 240 may further use skin temperature information, skin conductivity information, and/or blood pressure information to calculate a stress index. The stress index may increase, for example, if the heart rate increases, an interval between peaks of an electrocardiogram waveform decreases, the temperature of skin decreases, and the electrical conductivity of skin increases. The processor 240 may calculate a stress index by using a machine learning system, for example, a neural network or a support vector machine (SVM). The processor 240 may associate a time and a location at which the stress index was calculated, and/or a state of the user with the calculated stress index, and may store the stress index together with time information, location information, and/or state information.

According to an embodiment, the processor 240 may provide at least one activity of the repeated activities related to the user and the stress index corresponding to the at least one activity to the user, through the display 230 or the external electronic device. For example, the processor 240 may determine an activity of the activities, in which the location information pertains to a specified location range or the time information pertains to a specified time range as at least one activity. The processor 240 may display a map that represents at least one activity and a stress index corresponding to the at least one activity, through the display 230, at least based on the location information. According to an embodiment, the processor 240 may compare a first stress index at a first time corresponding to at least one activity and a second stress index at a second time, and may provide guide information determined at least based on the comparison result. The processor 240 may provide another activity associated with at least one activity as at least a part of the guide information. The processor 240 may transmit data related to the determined guide information to an external device operatively connected to the electronic device 200.

According to an embodiment, the processor 240 may provide the user with a stress index associated with time information, location information, and/or state information. For example, the processor 240 may display contents including an association relationship between the state information and the stress index on the display 230, or may provide contents to the external electronic device (e.g., the mobile device or the wearable device). For example, the processor 240 may provide a stress index associated with state information, together with the state information in the form of a table. As another example, the processor 240 may provide the stress index together with the location information and the state information in the form of a map. As another example, the processor 240 may provide the stress index together with the time information and the state information in the form of a graph.

According to an embodiment, the processor 240 may provide a change of the stress index according to a change of the state information to the user. For example, when a daily routine of the user is changed, the processor 240 may display an increase or a decrease of the stress index according to a change of the daily routine on the display 230.

According to an embodiment, the processor 240 may ignore or delete a part of the stress index, which is not associated with the state information. For example, the processor 240 may ignore or delete the stress index measured while the user performs an activity that is not determined as a daily routine of the user.

According to an embodiment, when the stress index is higher than a specified value, the processor 240 may provide a stress mitigating measure corresponding to state information associated with the stress to the user. The processor 240 may provide the user with various stress mitigating measures for management of the stress of the user. The processor 240 may store the stress mitigating measure mapped with the state information. When the stress index is higher than a specified value, the processor 240 may provide the user with a stress mitigating measure mapped with the state information corresponding to a time and/or a location at which a stress index that is higher than the specified value was measured, through the display 230 or the electronic device.

For example, if a stress index of a high strength is continuously recorded in a similar time band while the user is located at a site that is estimated as a workplace, the processor 240 may determine that the user is in a strong stress during work. In this case, the processor 240 may provide a message that recommends taking a walk or a change of a business environment to the user through the display 230 or the external electronic device.

As another example, if a stress index of a high strength is continuously recorded while the user is on a movement route, the processor 240 may determine that the user is in a strong stress while moving on a transportation means. In this case, the processor 240 may provide a message that recommends a change of a movement time band or a movement route to the user through the display 230 or the external electronic device.

As another example, when the stress index measured when the first activity is performed is high, the processor 240 may recommend a second activity that replaces the first activity to the user when the user performs the first activity later. For example, when a stress index measured when the user commutes to work on a public transportation, the processor 240 may recommend driving of a personal car to the user when the user commutes to work at the next time.

As another example, the processor 240 may store surrounding environment information (e.g., a weather) of a corresponding time point when a stress index measured when the first activity is performed, and may recommend a second activity that replaces the first activity to the user when the user is in a similar environment later.

As another example, if a stress index of a high strength is continuously recorded while the user is at home, the processor 240 may determine that the user is in a strong stress at home. The processor 240 may output a message that recommends taking a walk or an exercise through the display 230 if it is determined that an amount of the exercise of the user is insufficient based on the collected information, and may provide a message that recommends going out or taking a trip when it is determined that the frequency of going-out of the user is low through the display or the external electronic device.

As another example, when a sleeping time of the user is continuously insufficient, the processor 240 may provide a message that recommends an increase of the sleeping time or an exercise through the display 230 or the external electronic device.

As another example, if a stress index of a high strength is recorded while the user is talking on the phone by using the electronic device 200 (e.g., a wearable device) or another electronic device 200 (e.g., a smartphone), the processor 240 may provide a message that recommends stop of talking through the display 230 or the external electronic device.

According to an embodiment, when an activity by which the stress index is lowered is identified and the stress index is higher than a specified value, the processor 240 may provide the activity by which the stress index is lowered as a stress mitigating measure through the display 230. For example, when a low stress index is continuously detected after the user performs a walking movement or an exercise, the processor 240 may provide a message that recommends taking a walk or an exercise through the display 230 or the external electronic device if a stress index of a high strength is detected. The processor 240 may recommend a movement route on which a low stress index is detected to the user when the user is in a strong stress while moving.

According to an embodiment, the processor may control the external device 20 connected to the electronic device 200 to mitigate stress when a stress index is higher than a specified value. For example, the processor 240 may eject a flavoring agent by controlling a flavoring agent ejection device connected to the electronic device 200, and may reproduce music by controlling a music reproduction device connected to the electronic device 200.

As described above, the electronic device 200 may provide the user with information for easily recognizing a cause of stress by coupling state information on a daily routine of the user and a stress index, and may provide the user with a stress mitigating measure that is suitable for a situation in which a strong stress is present.

Hereinafter, an operation of obtaining state information will be described in detail with reference to FIGS. 3 and 4.

Figure 3:
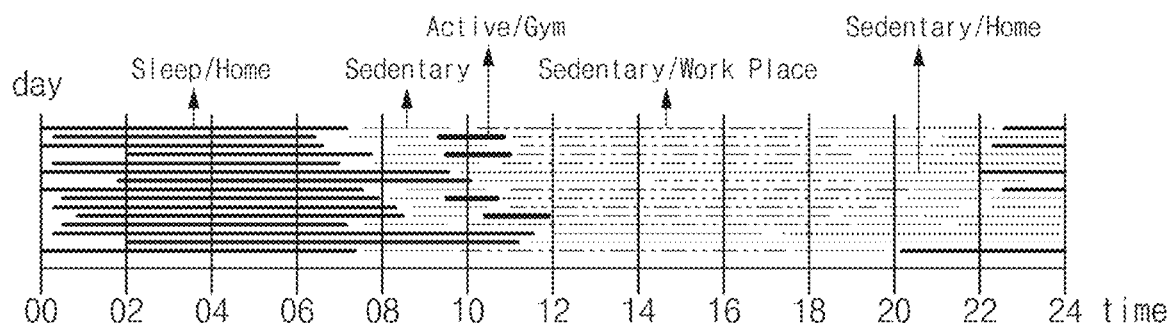
FIG. 3 is a graph illustrating an operation of obtaining state information by an electronic device according to an embodiment of the disclosure.

FIG. 3 is a graph illustrating an operation of obtaining state information by an electronic device according to an embodiment of the disclosure.

The graph of FIG. 3 depicts information on activities of the user obtained for 15 days by an electronic device (e.g., the processor 240 of the electronic device 200). According to an embodiment, the electronic device may obtain information for a plurality of activities performed by the user based on motion sensor information (e.g., acceleration sensor information), location information, and/or time information.

Referring to FIG. 3, the electronic device may identify activities such as sleeping, a movement by a car, an exercise, a task, and a rest. The electronic device may identify the activities by using atmospheric pressure information, surrounding temperature information, illumination intensity information, HR information, HRV information, angular speed information, skin temperature information, skin conductivity information, blood pressure information, blood glucose information, and/or blood flow rate information, as well as acceleration information and/or location information. The electronic device may obtain information on a time and a location at which an activity is performed. The electronic device may record information on the type of an activity (e.g., sleeping, a movement by a car, an exercise, a task, and a rest), a time at which the activity is performed, and a location at which the activity is performed.

Figure 4:
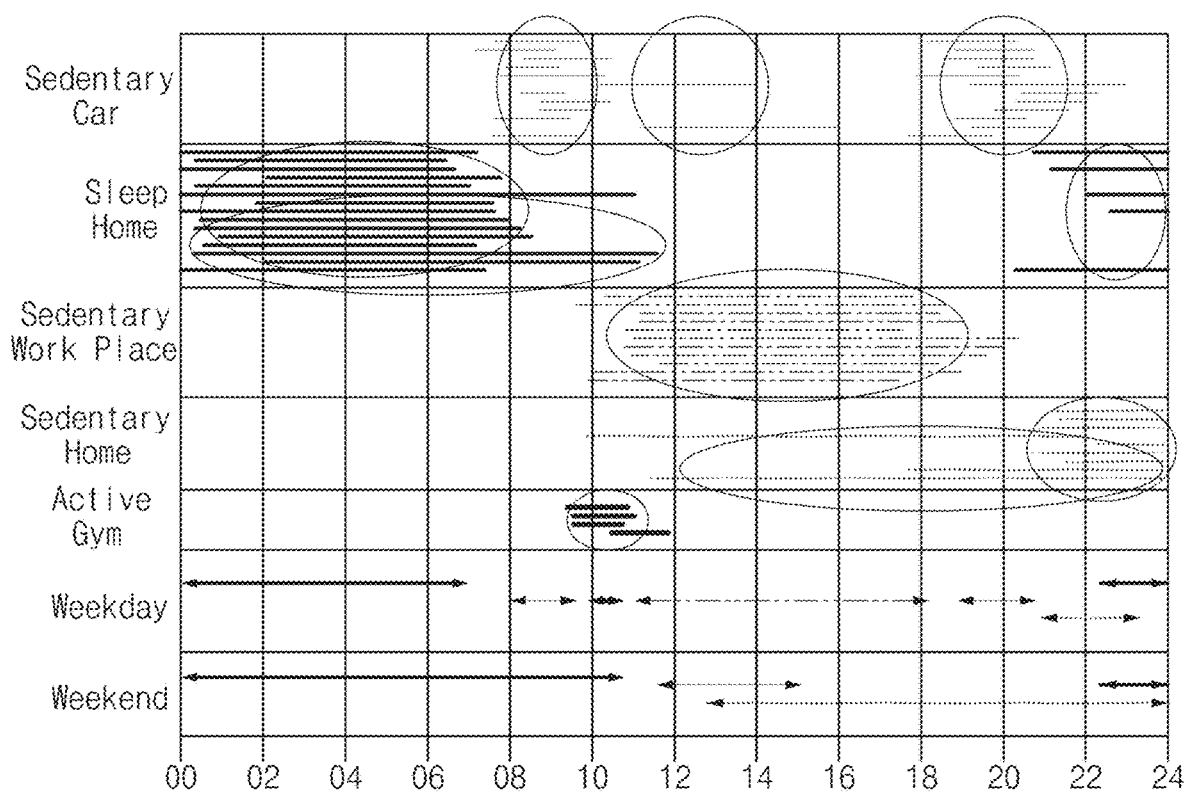
FIG. 4 is a graph illustrating an operation of obtaining state information by an electronic device according to an embodiment of the disclosure.

FIG. 4 is a graph illustrating an operation of obtaining state information by an electronic device according to an embodiment of the disclosure.

The graph of FIG. 4 depicts a process of extracting state information associated with a daily routine of the user based on information on the activity of FIG. 3. According to an embodiment, an electronic device (e.g., the processor 240 of the electronic device 200) may group activities, which have been performed in the same time band, of the activities, and may obtain state information associated with the grouped activities.

Referring to FIG. 4, the electronic device may group the corresponding activities when a deviation of the time band in which the same activities have been performed is smaller than a specified range. Because the daily routines of the user may be different on the weekdays and on the weekend, the electronic device may group the activities performed on the weekdays and may group the activities performed on the weekend. For example, the electronic device may identify sleeping at home at 22 to 7 on the weekdays, a movement in a car at 8 to 10, an exercise in a gymnasium at 10 to 11, a task in a workplace at 100 to 18, a movement in the car at 19 to 21, and a rest at home at 21 to 23 as daily routines of the user through grouping. As another example, the electronic device may identify sleeping at home at 22 to 11 on the weekdays, a movement in the car at 12 to 15, a rest at home at 13 to 24 as daily routines of the user through grouping. The electronic device may obtain state information on daily routines. The state information, for example, may include the type of an activity, a time at which the activity is mainly performed, and a site at which the activity is mainly performed.

Hereinafter, an operation of calculating a stress index will be described in detail with reference to FIGS. 5 and 6.

Figure 5:
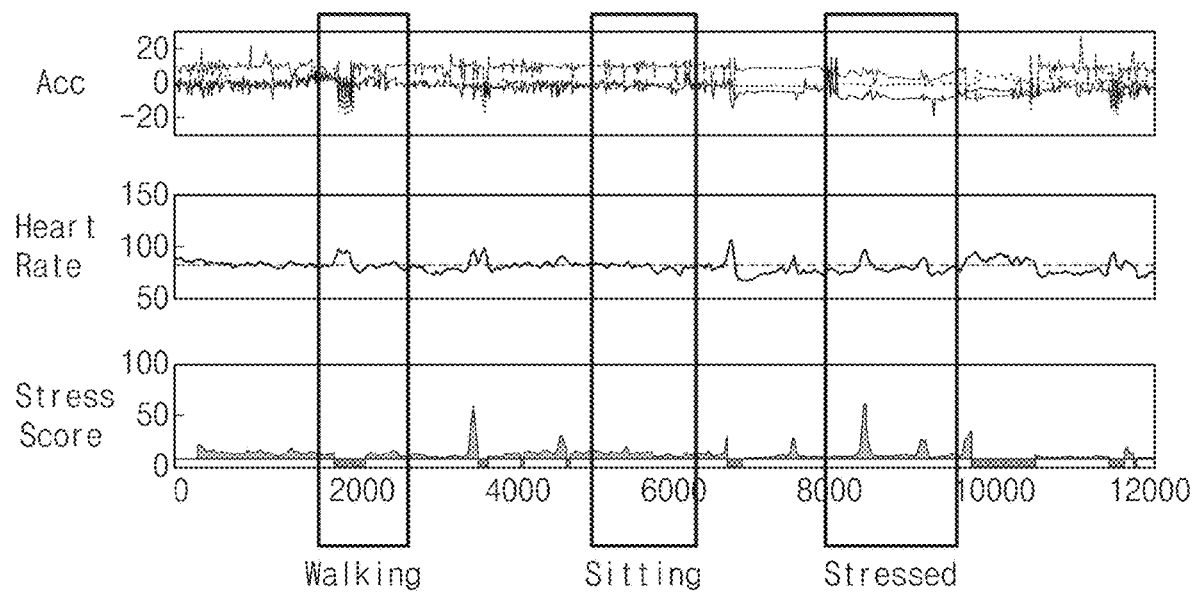
FIG. 5 is a graph illustrating an operation of calculating a stress index by an electronic device according to an embodiment of the disclosure.

FIG. 5 is a graph illustrating an operation of calculating a stress index by an electronic device according to an embodiment of the disclosure.

Referring to FIG. 5, an electronic device (e.g., the processor 240 of the electronic device 200) may obtain information by using a sensor module (e.g., the sensor module 210). For example, the electronic device may obtain biometric information (e.g., HR information) of the user by using a biometric sensor (e.g., the HR sensor), and may obtain information measured according to a movement of the user by using a motion sensor (e.g., the acceleration sensor or the gyro sensor). The electronic device may determine whether the user is in a sleeping state, an active state, or an inactive state, based on acceleration information. The electronic device may additionally use HR information and/or HRV information. For example, the electronic device may determine whether the user is in a waking movement state or the user is in a sitting state. The electronic device may calculate a stress index by using the HR information, the HRV information, and/or the blood pressure information of the user. The electronic device may record a stress index according to time.

Figure 6:
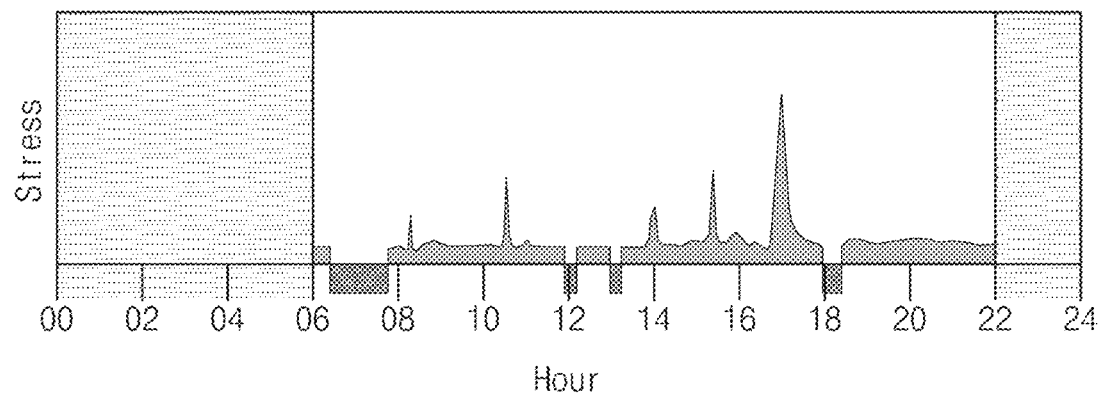
FIG. 6 is a graph illustrating an operation of calculating a stress index by an electronic device according to an embodiment of the disclosure.

FIG. 6 is a graph illustrating an operation of calculating a stress index by an electronic device according to an embodiment of the disclosure.

Referring to FIG. 6, an electronic device (e.g., the processor 240 of the electronic device 200) may determine whether the user is in a sleeping state, an active state, or an inactive state, and may record a stress index measured while the user is in an inactive state. When the user is in a sleeping state or an active state, the reliability of the measured stress index may be low due to a change of a heart rate due to sleeping or an activity, and because the user may experience stress of a high strength generally in an inactive state, the electronic device may calculate a stress index of only a period in which the user is in an inactive state. However, the disclosure is not limited thereto, but the electronic device may calculate a stress index while the user is in a sleeping state or an active state. The electronic device may record the stress index measured while the user is in an inactive state according to time.

Hereinafter, stress information provided by the electronic device will be described in detail with reference to FIGS. 7 to 9.

Figure 7:
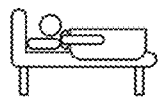
FIG. 7 illustrates contents including state information and a stress index provided by an electronic device according to an embodiment of the disclosure.
Figure 7:
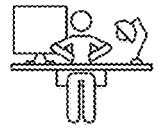
Figure 7:
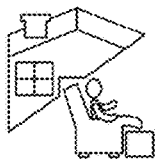
Figure 7:
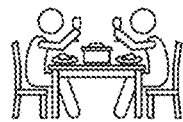
Figure 7:
Figure 7:

FIG. 7 illustrates contents including state information and a stress index provided by an electronic device according to an embodiment of the disclosure.

Referring to FIG. 7, an electronic device (e.g. the processor 240 of the electronic device 200) may provide a stress index associated with state information, together with the state information, to the display or the external electronic device. The electronic device may provide the state information and the stress index in the form of a table. For example, the electronic device may provide an icon associated with the obtained state information, and may provide the stress index matched with the state information besides the icon. The electronic device may provide a stress strength in a rest state, a stress strength in a driving state, a stress strength in a working state, and a stress strength in a meal state. In addition, the electronic device may further provide various pieces of information, such as a sleeping time and a sleeping efficiency in a sleeping state, and a predicted calorie consumption in an exercise state.

Figure 8:
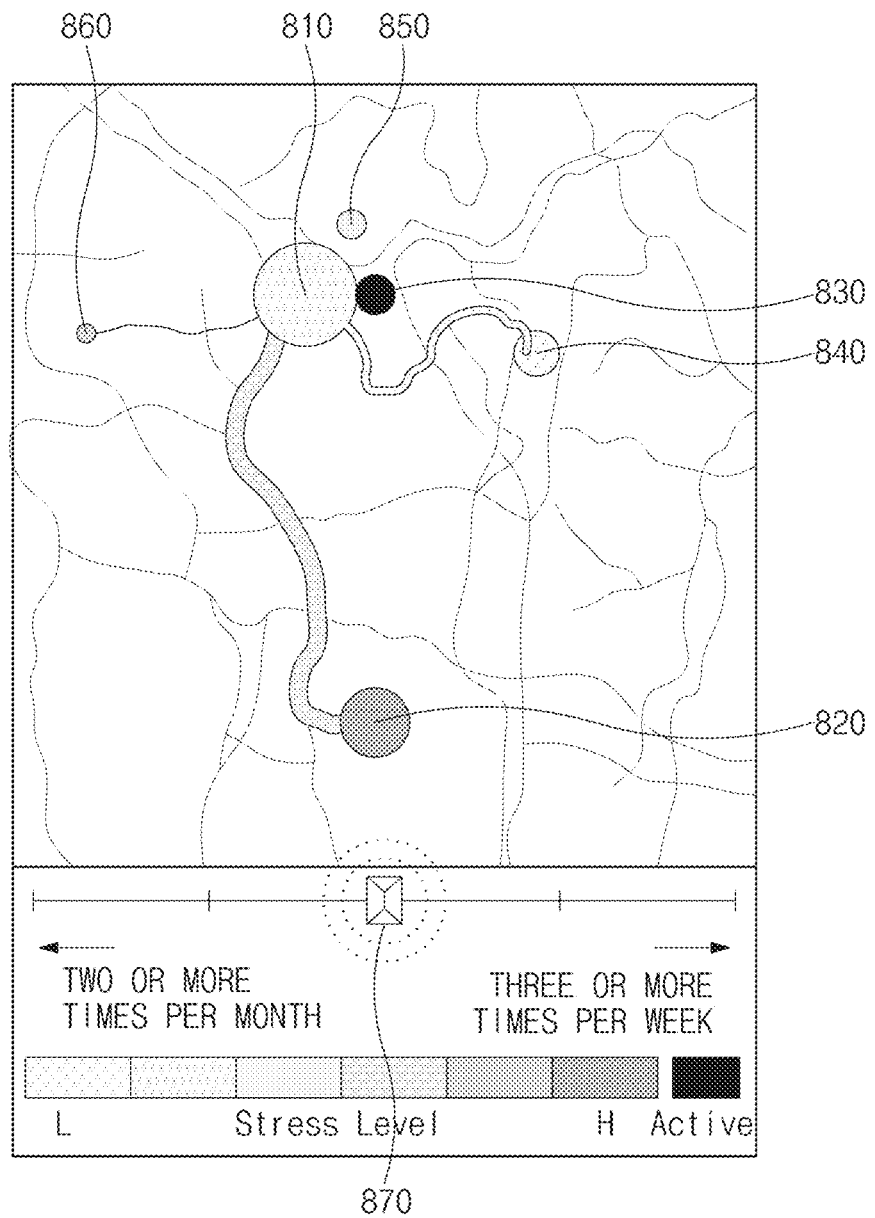
FIG. 8 illustrates a map including state information and a stress index provided by an electronic device according to an embodiment of the disclosure.

FIG. 8 illustrates a map including state information and a stress index provided by an electronic device according to an embodiment of the disclosure.

Referring to FIG. 8, an electronic device (e.g. the processor 240 of the electronic device 200) may provide a map that represents state information and stress information to the display or the external electronic device based on location information. For example, the electronic device may represent a value of a stress index by using a color that represents the stress index at a location at which the stress is measured. The value of the stress, for example, may be proportional to a concentration of a color. An area in which the user is in an active state may be indicated by a black color. The size of the area in which the stress index is displayed may be proportional to a time period for which the user stays in the corresponding area. The electronic device may represent only the stress index that is higher than a specified value on the map.

The first area 810, for example, may be the house of the user. The electronic device may indicate a first area 810 in which the user stays for a long time thickly, and may display the first area 810 in a bright color when the stress index in the first area 810 is low. The second area 820, for example, may be the workplace of the user. The electronic device may indicate a second area 820 thicker than the first area 810, and may indicate the second area 820 in a dark color when the stress index in the second area 820 is high. The area displayed between the first area 810 and the second area 820 may be a movement route of the user. The third area 830, for example, may be a gymnasium. The electronic device may determine the thickness of a third area 830 in proportion to a time period for which the user stays in the third area 830, and may indicate the third area 830 in a black color that represents an active state. In a similar manner, the electronic device may indicate a fourth area 840, a fifth area 850, a sixth area 860 which the user visited in the colors that represent the stress indices measured in the fourth area 840, the fifth area 850, and the sixth area 860.

According to an embodiment, the electronic device may set the repetition frequency of the activities that will be determined to be daily routines of the user by using the object 870 displayed below the map. The electronic device may change the frequency of repetitions if an object 870 is moved by a touch input to the object 870. For example, the electronic device may identify the activities repeated two or more times per month as daily routines if the frequency of the repetitions is set to two or more times per month, and may display the stress index corresponding to the identified daily routine on the map. As another example, the electronic device may identify the activities repeated three or more times per month as daily routines if the frequency of the repetitions is set to three or more times per month, and may display the stress index corresponding to the identified daily routine on the map.

Figure 9:
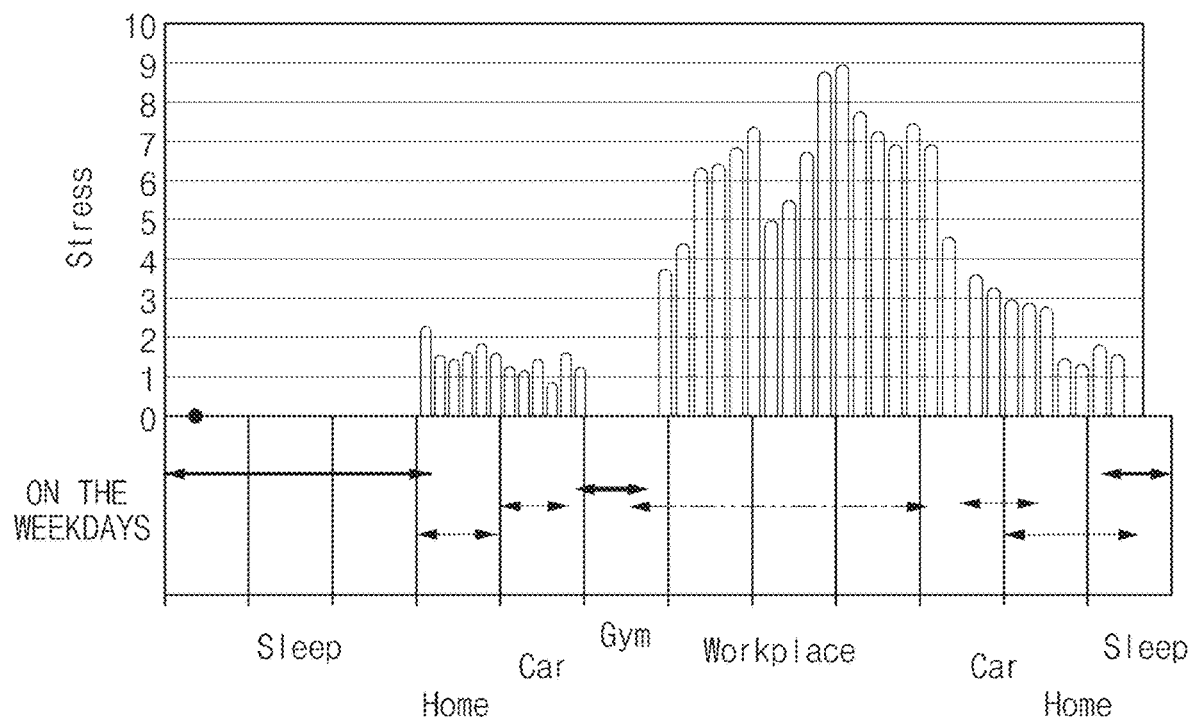
FIG. 9 illustrates a graph including state information and a stress index provided by an electronic device according to an embodiment of the disclosure.

FIG. 9 illustrates a graph including state information and a stress index provided by an electronic device according to an embodiment of the disclosure.

Referring to FIG. 9, an electronic device (e.g. the processor 240 of the electronic device 200) may provide a graph that represents state information and stress information to the display or the external electronic device according to time. For example, the electronic device may display state information and a line that represents a time band corresponding to the state information below the time axis of the graph. The electronic device may display the stress index measured while the user is in an inactive state according to time in the graph. Through the above-described graph, the stress indices corresponding to daily routines of the user may be easily recognized.

Figure 10:
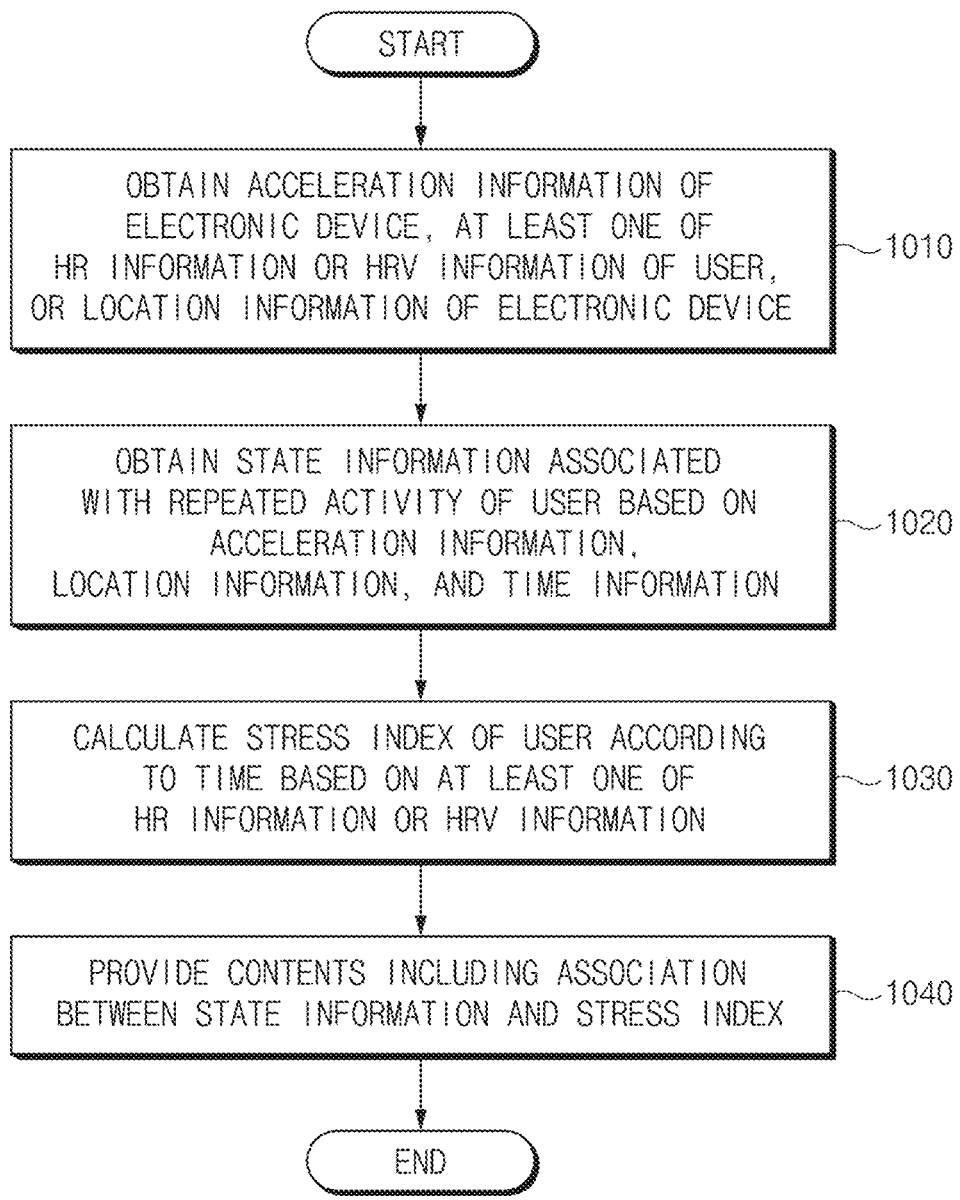
FIG. 10 is a flowchart illustrating a method for providing stress information of an electronic device according to an embodiment of the disclosure.

FIG. 10 is a flowchart illustrating a method for providing stress information of an electronic device according to an embodiment of the disclosure.

Hereinafter, it is assumed that the electronic device 200 of FIG. 2 performs a process of FIG. 10. Further, in a description of FIG. 10, an operation described to be performed by the electronic device may be understood to be controlled by the processor 240 of the device 200.

Referring to FIG. 10, in operation 1010, the electronic device may obtain acceleration information of the electronic device, at least one of HR information, HRV information, or blood pressure information of the user, and location information of the electronic device. The electronic device, for example, may obtain information related to a motion of the user by using the motion sensor, may obtain biometric information of the user by using the biometric sensor, and may obtain location information of the electronic device by using the communication circuit. The electronic device may obtain the above-described information from the external electronic device. For example, the electronic device may obtain various pieces of information for recognizing the daily routines of the user and calculating the stress. The electronic device may additionally obtain angular speed information, skin temperature information, skin conductivity information, blood pressure information, blood glucose information, and/or blood flow rate information.

In operation 1020, the electronic device may obtain state information associated with the repeated activity of the user based on acceleration information, location information, and time information. For example, the electronic device may identify an activity performed by the user based on at least a part of the collected information, may determine the repeatedly performed activity as a daily routine, and may obtain information on the type of the daily routine, a site and a route at which the daily routine was performed, and a time at which the daily routine was performed.

In operation 1030, the electronic device may calculate a stress index of the user according to time based on at least one of the HR information, the HRV information, or the blood pressure information. For example, the electronic device may calculate a stress index of the user based on at least a part of the collected information, and may record the calculated stress index together with the time information.

In operation 1040, the electronic device may provide contents that represent an association relationship between the state information and the stress information. For example, the electronic device may provide the state information and the stress index corresponding to the state information in various forms such as a table, a map, or a graph.

Figure 11:
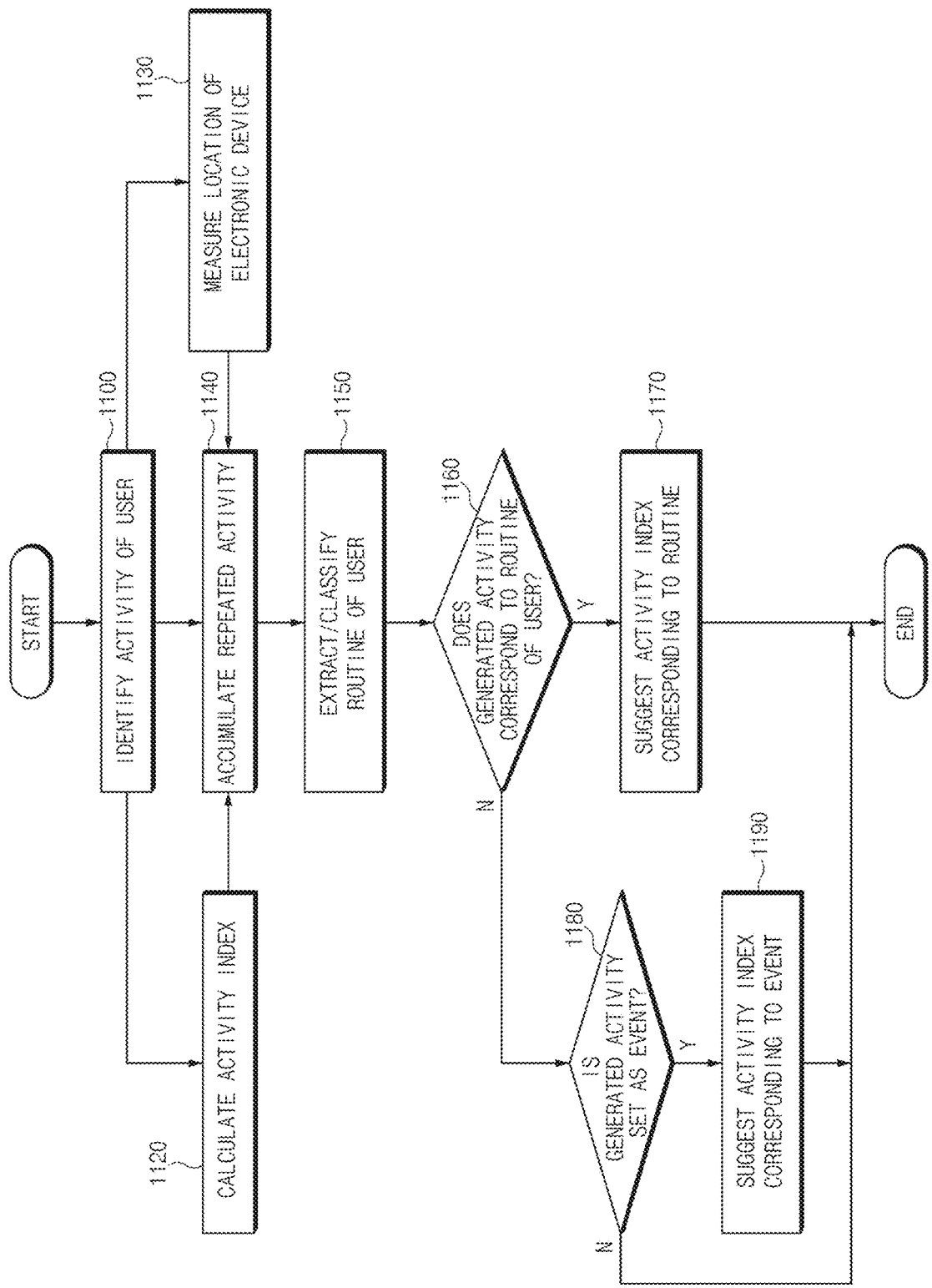
FIG. 11 is a flowchart illustrating a method for providing stress information of an electronic device according to an embodiment of the disclosure.

FIG. 11 is a flowchart illustrating a method for providing stress information of an electronic device according to an embodiment of the disclosure.

Hereinafter, it is assumed that the electronic device 200 of FIG. 2 performs a process of FIG. 11. Further, in a description of FIG. 11, an operation described to be performed by the electronic device may be understood to be controlled by the processor 240 of the device 200.

Referring to FIG. 11, in operation 1100, the electronic device may identify an activity of the user. For example, the electronic device may identify the activity of the user based on the information collected by the sensor module or the information received from the external electronic device.

In operation 1120, the electronic device may calculate the activity index of the user. For example, the electronic device may calculate an activity index including a stress index, a predicted calorie consumption, and a sleeping score based on the collected information.

In operation 1130, the electronic device may measure a location of the electronic device. For example, the electronic device may obtain location information of the electronic device based on the information collected by the communication module.

In operation 1140, the electronic device may accumulate a repeated activity. For example, the electronic device may consistently record information on the identified activity, an activity index, and location information.

In operation 1150, the electronic device may extract and classify the routine of the user. For example, the electronic device may extract the activities performed in the same band as the daily routines of the user, and may separate the daily routines according to the types of the activities.

In operation 1160, the electronic device may determine whether the generated activity corresponds to the routine of the user. For example, if an activity is generated, the electronic device may determine whether the corresponding activity corresponds to the extracted and separated routine.

When the activity corresponds to a routine of the user, in operation 1170, the electronic device may suggest an activity index corresponding to the routine to the user. For example, the electronic device may suggest contents including the type of the routine and the activity index corresponding to the routine to the user.

When the activity does not correspond to the routine of the user, in operation 1180, the electronic device may determine whether the generated activity is set as an event. For example, the electronic device may register the activity that is not included in the routine as an event according to a request of the user.

When the activity is set as an event, in operation 1190, the electronic device may suggest an activity index corresponding to the event. For example, the electronic device may suggest contents including an activity index measured during a time section in which the event is generated to the user.

Figure 12:
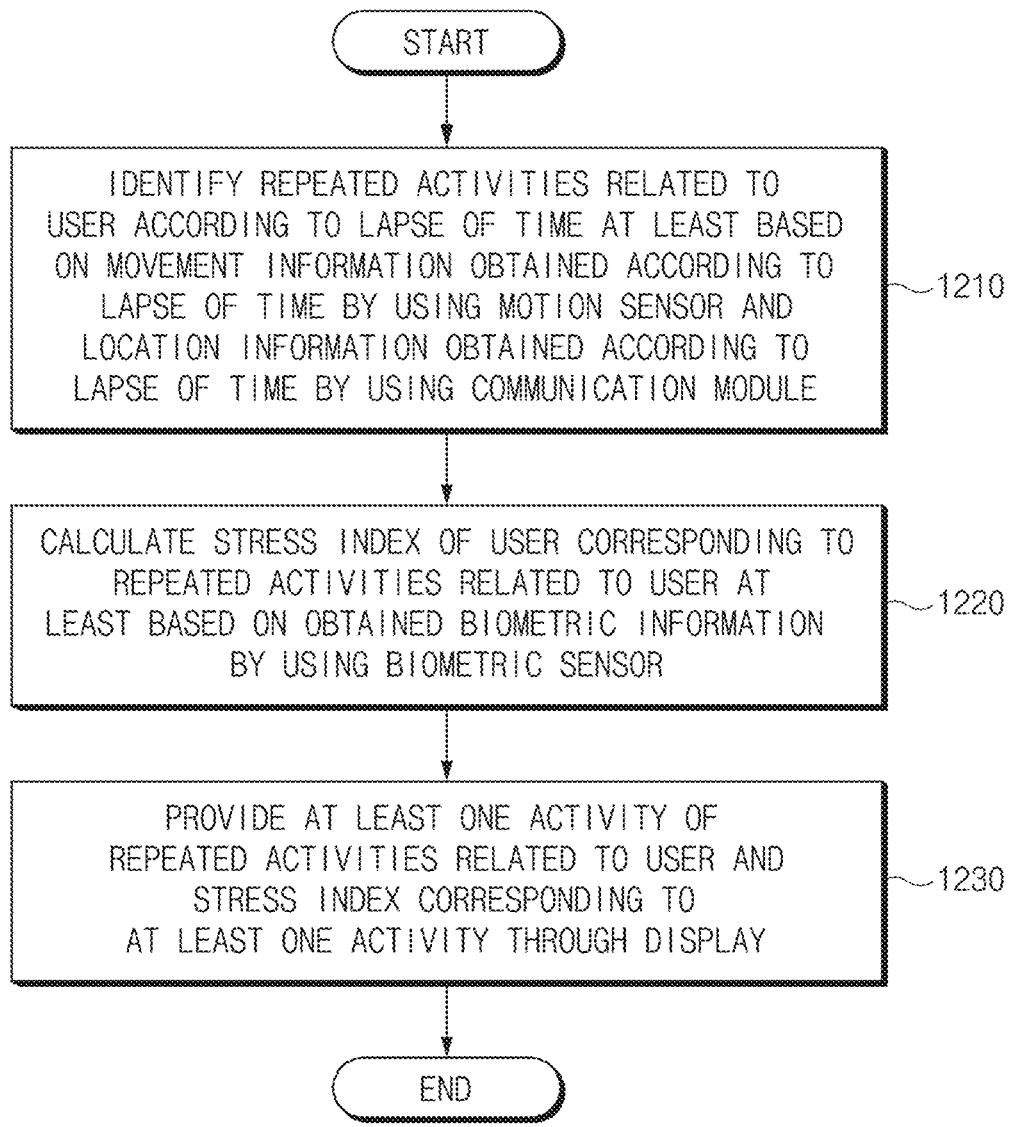
FIG. 12 is a flowchart illustrating a method for providing stress information of an electronic device according to an embodiment of the disclosure.

FIG. 12 is a flowchart illustrating a method for providing stress information of an electronic device according to an embodiment of the disclosure.

Hereinafter, it is assumed that the electronic device 200 of FIG. 2 performs a process of FIG. 12. Further, in a description of FIG. 12, an operation described to be performed by the electronic device may be understood to be controlled by the processor 240 of the device 200.

Referring to FIG. 12, in operation 1210, the electronic device may identify repeated activities related to the user according to lapse of time, at least based on movement information obtained according to lapse of time by using the motion sensor and location information obtained according to lapse of time by using the communication module. The repeated activities related to the user may include location information and time information corresponding top activities. The electronic device may determine the repeated activities further based on biometric information. According to an embodiment, the electronic device may store surrounding environment information of the electronic device in association of the repeated activities related to the user.

In operation 1220, the electronic device may calculate the stress index of the user corresponding to the repeated activities related to the user at least based on the obtained biometric information by using the biometric sensor. The biometric sensor may include the HR sensor. The electronic device may determine a stress index, based on at least one of the HR information or the HRV information of the user obtained by using the HR sensor.

In operation 1230, the electronic device may provide at least one of the repeated activities related to the user and a stress index corresponding to the at least one activity, through the display. For example, the electronic device may determine an activity of the repeated activities, in which the location information pertains to a specified location range or the time information pertains to a specified time range as at least one activity. The electronic device may display a map that represents at least one activity and a stress index corresponding to the at least one activity, through the display, at least based on the location information. According to an embodiment, the electronic device may compare a first stress index at a first time corresponding to at least one activity and a second stress index at a second time, and may provide guide information determined at least based on the comparison result. The electronic device may provide another activity associated with at least one activity as at least a part of the guide information. The electronic device may transmit data related to the determined guide information to an external electronic device operatively connected to the electronic device.

The electronic device according to various embodiments disclosed in the disclosure may be various types of devices. The electronic device may include, for example, at least one of a portable communication device (e.g., a smartphone), a computer device, a portable multimedia device, a mobile medical appliance, a camera, a wearable device, or a home appliance. The electronic device according to an embodiment of the disclosure should not be limited to the above-mentioned devices.

It should be understood that various embodiments of the disclosure and terms used in the embodiments do not intend to limit technologies disclosed in the disclosure to the particular forms disclosed herein; rather, the disclosure should be construed to cover various modifications, equivalents, and/or alternatives of embodiments of the disclosure. With regard to description of drawings, similar components may be assigned with similar reference numerals. As used herein, singular forms may include plural forms as well unless the context clearly indicates otherwise. In the disclosure disclosed herein, the expressions "A or B", "at least one of A or/and B", "A, B, or C" or "one or more of A, B, or/and C", and the like used herein may include any and all combinations of one or more of the associated listed items. The expressions "a first", "a second", "the first", or "the second", used in herein, may refer to various components regardless of the order and/or the importance, but do not limit the corresponding components. The above expressions are used merely for the purpose of distinguishing a component from the other components. It should be understood that when a component (e.g., a first component) is referred to as being (operatively or communicatively) "connected," or "coupled," to another component (e.g., a second component), it may be directly connected or coupled directly to the other component or any other component (e.g., a third component) may be interposed between them.

The term "module" used herein may represent, for example, a unit including one or more combinations of hardware, software and firmware. The term "module" may be interchangeably used with the terms "logic", "logical block", "part" and "circuit". The "module" may be a minimum unit of an integrated part or may be a part thereof. The "module" may be a minimum unit for performing one or more functions or a part thereof. For example, the "module" may include an application-specific integrated circuit (ASIC).

Various embodiments of the disclosure may be implemented by software (e.g., the program 140) including an instruction stored in a machine-readable storage media (e.g., an internal memory 136 or an external memory 138) readable by a machine (e.g., a computer). The machine may be a device that calls the instruction from the machine-readable storage media and operates depending on the called instruction and may include the electronic device (e.g., the electronic device 101). When the instruction is executed by the processor (e.g., the processor 120), the processor may perform a function corresponding to the instruction directly or using other components under the control of the processor. The instruction may include a code generated or executed by a compiler or an interpreter. The machine-readable storage media may be provided in the form of non-transitory storage media. Here, the term "non-transitory", as used herein, is a limitation of the medium itself (i.e., tangible, not a signal) as opposed to a limitation on data storage persistency.

According to an embodiment, the method according to various embodiments disclosed in the disclosure may be provided as a part of a computer program product. The computer program product may be traded between a seller and a buyer as a product. The computer program product may be distributed in the form of machine-readable storage medium (e.g., a compact disc read only memory (CD-ROM)) or may be distributed only through an application store (e.g., a Play Store™). In the case of online distribution, at least a portion of the computer program product may be temporarily stored or generated in a storage medium such as a memory of a manufacturer's server, an application store's server, or a relay server.

Each component (e.g., the module or the program) according to various embodiments may include at least one of the above components, and a portion of the above sub-components may be omitted, or additional other sub-components may be further included. Alternatively or additionally, some components (e.g., the module or the program) may be integrated in one component and may perform the same or similar functions performed by each corresponding components prior to the integration. Operations performed by a module, a programming, or other components according to various embodiments of the disclosure may be executed sequentially, in parallel, repeatedly, or in a heuristic method. Also, at least some operations may be executed in different sequences, omitted, or other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   a display;
   a biometric sensor configured to obtain biometric information of a user of the electronic device;
   a motion sensor configured to obtain motion information of the electronic device;
   a communication circuit configured to receive a signal for determining location information of the electronic device; and
   a processor electrically connected with the display, the biometric sensor, the motion sensor, and the communication circuit,
   wherein the processor is configured to:
      identify a group of activities related to the user, over a same time band, based on the motion information obtained over the same time band using the motion sensor and the location information determined over the same time band using the signal received by the communication circuit, wherein the group of activities comprises repeated activities performed within the same time band as a part of a daily routine,
      calculate a stress index of the user corresponding to the group of activities related to the user based on the biometric information obtained using the biometric sensor,
      associate the stress index of the user with the group of activities, and
      provide, via the display,
   contents including an association between the stress index of the user and the group of activities.

2. The electronic device of claim 1,
   wherein the repeated activities related to the user include the location information and time information corresponding to the repeated activities, and
   wherein the processor is further configured to:
      group corresponding activities as the group of activities when a deviation of a time band in which same activities have been performed is smaller than a specified range.

3. The electronic device of claim 1, wherein the processor is further configured to:
   display, on the display, a map based on the location information, the map representing the repeated activities and the stress index corresponding to the repeated activities, as at least a part of the contents.

4. The electronic device of claim 1,
   wherein the biometric sensor includes a heart rate (HR) sensor, and
   wherein the processor is further configured to:
      calculate the stress index, based on at least one of HR information or heart rate variability (HRV) of the user obtained using the HR sensor.

5. The electronic device of claim 1, wherein the processor is further configured to:
   identify the repeated activities, further based on the biometric information.

6. The electronic device of claim 1, wherein the processor is further configured to:
   compare a first stress index at a first time and a second stress index at a second time corresponding to an activity, and
   provide guide information related to the activity determined at least based on a comparison result.

7. The electronic device of claim 6, wherein the processor is further configured to:
   provide, via the display, another activity associated with the activity as at least a part of the guide information.

8. The electronic device of claim 6, wherein the processor is further configured to:
   transmit data related to the provided guide information to an external electronic device operatively connected to the electronic device.

9. The electronic device of claim 1, wherein the processor is further configured to:
   store surrounding environment information of the electronic device in association with the repeated activities related to the user.

10. An electronic device comprising:
   a sensor module including an acceleration sensor and a heart rate (HR) sensor;
   a communication circuit configured to receive a signal for determining a location of the electronic device;
   a display; and
   a processor electrically connected with the sensor module, the communication circuit, and the display,
   wherein the processor is configured to:

determine location information of the electronic device over a same time band using the signal received by the communication circuit, obtain acceleration information of the electronic device over the same time band and at least one of HR information over the same time band or heart rate variability (HRV) information of a user of the electronic device over the same time band, using the sensor module, obtain state information associated with a group of activities of the user of the electronic device based on the location information and the acceleration information over the same time band, wherein the group of activities comprises repeated activities performed within the same time band as a part of a daily routine, calculate a stress index of the user of the electronic device over the same time band based on at least one of the HR information or the HRV information, associate the state information and the stress index over the same time band, and provide content including an association between the state information and the stress index to the display or an external electronic device.

11. The electronic device of claim 10, wherein the processor is further configured to:

obtain the state information over the same time band based on the acceleration information, at least one of the HR information or the HRV information, and the location information over the same time band.

12. The electronic device of claim 10, wherein the sensor module further includes a gyro sensor, and wherein the processor is further configured to:
obtain angular speed information of the electronic device using the gyro sensor, and
obtain the state information based on the acceleration information, the angular speed information, and the location information over the same time band.

13. The electronic device of claim 10, wherein the processor is further configured to:

determine whether a user of the electronic device is in a sleeping state, an active state, or an inactive state based on the acceleration information, at least one of the HR information or the HRV information, or the location information over the same time band, and obtain the state information based on whether the user of the electronic device is in the sleeping state, the active state, or the inactive state repeatedly for a time band within a specified range.

14. The electronic device of claim 10, wherein the processor is further configured to:

if the user of the electronic device repeatedly performs a same activity a specified number of times or more for a time period of a specified range, obtain the state information associated with the same activity.

15. The electronic device of claim 10, wherein the processor is further configured to:

obtain information on a plurality of activities performed by the user of the electronic device based on the acceleration information, the location information, and time information, group activities as the group of activities for the same time band, which are performed at a same time of day, of the plurality of activities, and obtain the state information associated with the group of activities.

16. The electronic device of claim 10, wherein the processor is further configured to:

provide the stress index associated with the state information, together with the state information, to the display or the external electronic device.

17. The electronic device of claim 10, wherein the processor is further configured to:

provide, to the display or the external electronic device, a map based on the location information, the map representing the state information and the stress index corresponding to the state information.

18. The electronic device of claim 10, wherein the processor is further configured to:

determine if the stress index is higher than a specified value, and if the stress index is higher than the specified value, provide a solution to stress corresponding to the state information to the display or the external electronic device.

19. The electronic device of claim 10, wherein the processor is further configured to:

determine if the stress index is higher than a specified value, and if the stress index is higher than the specified value, control an external device connected to the electronic device to mitigate stress.

20. An electronic device comprising:

a communication circuit configured to communicate with an external device; and a processor that is electrically connected to the communication circuit, wherein the processor is configured to:
obtain acceleration information of the external device over a same time band, at least one of heart rate (HR) information over the same time band, or heart rate variability (HRV) information of a user of the external device over the same time band, and location information of the external device, obtain state information associated with a group of activities of the user of the external device based on the acceleration information and
the location information over the same time band, wherein the group of activities comprises repeated activities performed within the same time band as a part of a daily routine, calculate a stress index of the user of the external device over the same time band based on at least one of the HR information or the HRV information, associate the state information and the stress index over the same time band, and provide, to at least one of a display of the electronic device, the external device, or another external device, displayable content including an association between the state information and the stress index.

* * * * *